(12) United States Patent
Dunlop et al.

(10) Patent No.: US 7,387,608 B2
(45) Date of Patent: Jun. 17, 2008

(54) APPARATUS AND METHOD FOR THE TREATMENT OF SLEEP RELATED DISORDERS

(76) Inventors: David A Dunlop, 3501 County Road 464, Elgin, TX (US) 78621; Robert Dale Gunderman, Jr., 4149 Clover St., Honeoye Falls, NY (US) 14472

( * ) Notice: Subject to any disclaimer, the term of this patent is extended or adjusted under 35 U.S.C. 154(b) by 228 days.

(21) Appl. No.: 11/098,800

(22) Filed: Apr. 5, 2005

(65) Prior Publication Data
US 2005/0222503 A1    Oct. 6, 2005

Related U.S. Application Data

(60) Provisional application No. 60/559,914, filed on Apr. 6, 2004.

(51) Int. Cl.
*A61B 5/02*    (2006.01)
*A61B 5/00*    (2006.01)

(52) U.S. Cl. .................. 600/500; 600/483; 600/323; 600/324

(58) Field of Classification Search ............. 600/481, 600/483, 500–504, 300, 301, 323–340
See application file for complete search history.

(56) References Cited

U.S. PATENT DOCUMENTS

| | | | |
|---|---|---|---|
| 4,655,213 A | 4/1987 | Rapoport et al. | |
| 4,765,340 A | 8/1988 | Sakai et al. | |
| 4,773,411 A | 9/1988 | Downs | |
| 5,190,038 A | 3/1993 | Polson et al. | |
| 5,398,682 A | 3/1995 | Lynn | |
| 5,605,151 A | 2/1997 | Lynn | |
| 5,842,978 A * | 12/1998 | Levy | ........................ 600/300 |
| 6,331,536 B1 | 12/2001 | Radulovacki et al. | |
| 6,537,228 B1 | 3/2003 | Lambert | |
| 6,539,940 B2 | 4/2003 | Zdrojkowski et al. | |
| 6,760,608 B2 | 7/2004 | Lynn | |
| 2002/0190863 A1* | 12/2002 | Lynn | ...................... 340/573.1 |
| 2005/0101833 A1 | 5/2005 | Hsu et al | |
| 2006/0097879 A1 | 5/2006 | Lippincott | |

OTHER PUBLICATIONS

National Sleep Foundation web site page entitled "How is Sleep Apnea Treated" Dated Feb. 17, 2004. http://www.sleepfoundation.org/publications/sleepap.cfm 3 pages.
Sleep Heart Study Home page Dated Sep. 20, 2005. http://www.jhucct.com/shhs/default.html 1 page.
Sleep Heart Study web site page entitled "Design" Dated Sep. 20, 2005. http://www.jhucct.com/shhs/details/design.htm 4 pages.

* cited by examiner

*Primary Examiner*—Charles A. Marmor, II
*Assistant Examiner*—Navin Natnithithadha (57) ABSTRACT

An apparatus to detect the onset of sleep apnea, and to provide an automated way to awaken the sleeping patient at the onset of sleep apnea. The apparatus may also contain a recording device or computer that captures blood oxygen levels and pulse rates throughout the period of sleep, and may contain computer programs, algorithms, subroutines or logic to determine the level of blood oxygen and pulse rate that indicates the onset of a sleep apnea event. The method of arousing the patient from sleep at the onset of a sleep apnea event will decrease or eliminate the occurrence of sleep apnea, arrhythmia, and partial epilepsy over time.

7 Claims, 5 Drawing Sheets

APPARATUS AND METHOD FOR THE TREATMENT OF SLEEP RELATED DISORDERS

CROSS-REFERENCE TO RELATED PATENT APPLICATIONS

This application claims the benefit of the filing date of U.S. Provisional patent application U.S. Ser. No. 60/559,914 filed on Apr. 6, 2004.

BACKGROUND OF THE INVENTION

1. Field of the Invention

The present invention relates to an apparatus to detect and prevent the occurrence of sleep apnea, and a method of preventing the occurrence and continuation of sleep apnea related events. The present invention also detects, prevents and cures certain forms of arrhythmia and partial epilepsy.

2. Description of the Prior Art

Sleep Apnea is a breathing disorder that occurs during periods of sleep. The Greek word "apnea" means "without breath". It is an intermittent cessation of ventilation during sleep that results in a decrease in blood oxygen levels, a decrease in heart rate, and resultant illnesses such as cardiac arrhythmias, hypertension, heart disease, and/or heart failure. The consequences of sleep apnea are evident throughout the waking hours, and include sleepiness, non-attentiveness, headaches, memory problems, weight gain, safety-related accidents, personality disturbances, and other sleep-deprivation related afflictions. The causes of the various forms of sleep apnea are not fully understood. There are three general types of sleep apnea: Obstructive, Central and Mixed.

Obstructive sleep apnea results from a blockage or occlusion of the oropharyngeal (upper) airway. With obstructive sleep apnea, respiratory functions continue, but blockage or occlusion of the airway results in reduced or halted airflow. The increased airflow resistance is typically caused by an anatomical or functional abnormality of the upper airway. These abnormalities have been known to include a displacement of the tongue during sleep, muscle disjunction in the upper airway dilator muscles, and excessive soft tissue in the neck that causes undue pressure on the airway structure (typically occurring in obese patients). Also, the act of snoring usually aggravates the narrowing of the upper airway through the production of edema in the soft tissues. Obstructive sleep apnea syndrome is indicated by a narrowing of the upper airway, resulting in a progressive asphyxia that continues until the individual is briefly woken from sleep, which restores airway patency and airflow through the upper airway. These frequent arousals, although necessary for proper airway ventilation to resume, deprive the individual from restorative deep sleep. These partial awakenings throughout sleep result in both mental and physical strain on the individual. Obstructive sleep apnea is the most common form of sleep apnea.

Central sleep apnea results from the brain failing to signal the muscles to breathe. The neural drive to the respiratory muscles discontinues for a brief period of time. These transients may continue throughout the night for periods from ten seconds to as long as 2 to 3 minutes. Central sleep apnea results from respiratory neuromuscular and metabolic control abnormalities or transient defects related to the respiratory control system. Often times individuals with central sleep apnea have a history of pulmonary hypertension, heart disease or heart failure, respiratory problems, or polycythemia. Central sleep apnea, similar to obstructive sleep apnea, causes a gradual asphyxiation during sleep, resulting is a brief arousal from sleep, at which time the individual's respiratory function returns to normal. Similar to obstructive sleep apnea, central sleep apnea can result in illnesses such as cardiac arrhythmias, hypertension, heart disease and/or heart failure. The consequences of central sleep apnea during the waking hours is similar to those of obstructive sleep apnea, and include sleepiness, non-attentiveness, headaches, memory problems, weight gain, safety-related accidents, personality disturbances, and other sleep-deprivation related afflictions.

Mixed sleep apnea is a combination of obstructive sleep apnea and central sleep apnea.

There are several known treatments for sleep apnea. They consist of physical or mechanical treatments, surgery, and attempts at pharmacological treatment. The treatment regimen is tailored to the individual, and is based on the medical profile of the patient being treated.

The most common effective treatment for patients with sleep apnea is nasal continuous positive airway pressure (CPAP). In this form of treatment, the patient wears a mask over the nose while sleeping. The mask is connected to a compressor that creates a positive pressure in the nasal passages. The continuous positive airway pressure system prevents the airway from closing or becoming obstructed during sleep. The air pressure from the continuous positive airway system is constant, and can be adjusted to best suit the individual's apnea condition. The air pressure in the continuous positive airway pressure system must be adjusted so that it maintains an open airway in the patient during all periods of sleep, but does not provide excessive pressure such that the device is bothersome to the patient. U.S. Pat. No. 4,655,213 discloses sleep apnea treatments based on the principles of continuous positive airway pressure. There have also been recent attempts at varying the applied pressure to increase the effectiveness of continuous positive airway pressure treatment. U.S. Pat. Nos. 4,773,411 and 6,539,940 disclose such techniques. The disclosures of these Unites States patents are incorporated herein by reference.

Continuous positive airway pressure systems remain the most effective treatment for sleep apnea. Many patients, however, cannot tolerate the positive airway pressure systems and associated apparatus. Common complaints include discomfort with the applied pressure, discomfort with the mask and equipment, nasal irritation, nasal stuffiness and congestion, airway dryness, mask air leaks and noise, noise of the CPAP machine, headaches, abdominal bloating, sore and irritated eyes, and an overall discomfort with the machinery. The noise and general obtrusiveness of the CPAP apparatus are often disruptive to another person sleeping with the user.

Another treatment for sleep apnea in certain patients involves the use of a dental appliance to reposition oral structures such as the tongue and the lower jaw. This form of treatment is typically performed by a dentist or dental specialist such as an orthodontist.

Surgery has also been performed to treat sleep apnea. In some surgical treatments, the size of the airway is increased. These surgical procedures contain elevated levels of risk in comparison to other treatment methods, and often times are not entirely effective. The form of surgery to be undertaken is specific to the patient and the patient's medical profile. The removal of obstructive tissue in the airway such as adenoids, tonsils or nasal polyps is a common form of surgical treatment for sleep apnea. The surgical correction of structural deformities is also a common form of surgical treatment for sleep apnea.

Another form of surgical treatment for sleep apnea is uvalopalatopharyngoplasty. This procedure removes excess tissue from the back of the throat, such as tonsils, uvula, and part of the soft palate. Somnoplasty is also being investigated as a possible treatment for sleep apnea. Somnoplasty uses radio waves to reduce the size of some airway structures such as the uvula and the back of the tongue.

Other forms of surgical intervention for sleep apnea include maxillo-facial reconstruction. Another form of surgical treatment for patients with severe and life threatening sleep apnea is Tracheostomy. This procedure involves making a small hole in the windpipe that accommodates a tube. The tube is opened only during sleep, and allows a patient to take air directly into the lungs, effectively bypassing any upper airway obstructions. Tracheostomy is an extreme procedure that is very rarely used except for cases of imminent life threatening sleep apnea.

Pharmacological treatments for sleep apnea have not generally been proven to be effective. Attempts at pharmacological treatment for sleep apnea have included respiratory stimulants such as theophylline, acetazolamide and medroxyprogesterone, and adenosine. Drugs that stimulate brain or central nervous system activity, such as naloxone and doxapram, have also been used in an attempt to treat sleep apnea. Other drugs that act on the neurotransmitters involved with respiration have also been used in an attempt to treat sleep apnea. These drugs include serotonin, dopamine, tryptophan, fluoxetine, and others. These pharmacological treatments for sleep apnea have not achieved any consistent levels of effectiveness, and often contain side effects.

Of the various treatments available for sleep apnea today, Continuous Positive Airway Pressure Systems have proven to be the most effective. Unfortunately, many patients cannot tolerate Continuous Positive Airway Pressure Systems. This leaves many sleep apnea patients without an effective treatment regimen.

There is therefore a need for a treatment for sleep apnea that does not involve the use of a complicated apparatus, and that does not include the use of pharmaceuticals.

Accordingly, embodiments of the present invention are provided that meet at least one or more of the following objects of the present invention. It is an object of this invention to provide an apparatus that detects and prevents the occurrence of sleep apnea, and also detects, prevents and cures certain forms of arrhythmia and partial epilepsy.

It is a further object of this invention to provide a method for treating sleep apnea, that reduces or eliminates the condition of sleep apnea in the patient.

It is a further object of this invention to provide an apparatus and a method for the monitoring and treatment of Sudden Infant Death Syndrome (SIDS).

It is a further object of this invention to provide an apparatus and a method for the treatment of snoring.

BRIEF SUMMARY OF THE INVENTION

In accordance with the present invention, there is provided an apparatus for the treatment of sleep apnea comprising a pulse-oximeter, a pulse-oximeter probe connected to the pulse-oximeter, a means for detecting an increase in pulse and a decrease in blood oxygen content as measured by the pulse-oximeter, and alarm means that is activated upon an increase in said pulse and a decrease in said blood oxygen content.

In accordance with the present invention, there is further provided a method for the treatment of sleep apnea comprising the steps of connecting a pulse-oximeter probe to said patient, connecting a pulse-oximeter probe to said pulse-oximeter, monitoring blood oxygen level and pulse rate of said patient using the pulse-oximeter, establishing threshold values for blood oxygen level values and pulse values at which to activate an alarm warning of the onset of said sleep apnea in said patient, activating said alarm at the onset of said sleep apnea in said patient as indicated by said blood oxygen level and said pulse rate of said patient reaching said threshold values. The method for the treatment of sleep apnea, in some embodiments, may further include the steps of collecting said blood oxygen level data and said pulse rate data from said patient, generating a comparison between said blood oxygen level data and said pulse rate data from said patient to baseline data for blood oxygen level and pulse rate, and modifying said threshold values for said blood oxygen level and said pulse rate based on said comparison.

BRIEF DESCRIPTION OF THE DRAWINGS

The invention will be described by reference to the following drawings, in which like numerals refer to like elements, and in which.

The present invention will be described in connection with a preferred embodiment, however, it will be understood that there is no intent to limit the invention to the embodiment described. On the contrary, the intent is to cover all alternatives, modifications, and equivalents as may be included within the spirit and scope of the invention as defined by the appended claims.

DESCRIPTION OF THE PREFERRED EMBODIMENTS

For a general understanding of the present invention, reference is made to the drawings. In the drawings, like reference numerals have been used throughout to designate identical elements.

In accordance with this invention there is provided an apparatus and method for the treatment of sleep apnea and other sleep disorders, arrhythmia and partial epilepsy. In one embodiment of the invention, the blood oxygen level and the pulse rate of the patient are monitored during sleep by the apparatus, which acts as a monitoring system to detect and warn of impending sleep apnea in the patient. The monitoring system is comprised of a pulse-oximeter, a computer and software program, and an external alarm such as a bell, horn, radio, or electronic alert.

At the onset of sleep apnea, the patient's blood oxygen level decreases, with a corresponding increase in heart rate (also described herein as pulse rate). The increase in heart rate and decrease in blood oxygen level is an indicator of the onset of sleep apnea. During sleep, it is normal for one's heart rate and blood oxygen level to vary. Discerning between normal variations in heart rate and blood oxygen levels during sleep and variations in heart rate and blood oxygen levels that are indicative of the onset of sleep apnea is performed using a software program that dynamically adapts to the patient to accurately identify the onset of sleep apnea and eliminate false alarms.

The software program monitors the combined increase in heart rate and decrease in blood oxygen level, and dynamically adjusts the alarm thresholds for pulse rate and blood oxygen level, or a combination thereof. The pulse rate and blood oxygen level thresholds that indicate the onset of sleep apnea can be initially programmed, and then subsequently adjusted for each patient. These pulse rate and blood oxygen level thresholds are monitored and dynamically adjusted during the treatment regimen by use of a software program. The dynamic adjustment of these thresholds serves to reduce the incidence of false alarms, and to improve the accuracy of sleep apnea detection.

The present invention may use historical data, software programs, algorithms or subroutines to assist with the determination of thresholds that are appropriate to the patient. When the patient's pulse rate and blood oxygen levels cross these pre-established thresholds during sleep, a waking alarm is triggered that activates some type of alert mechanism such as a bell, radio or electronic alert. The alert mechanism may be audible, mechanical, or of any type of stimulus that provides an awakening event. When the alarm goes off during sleep, the patient is partially awakened, sufficiently to interrupt the sleep apnea. This arousal of the patient from sleep stops the sleep apnea condition.

Upon being subjected to repeated sleep apnea incidents while using the apparatus of the present invention, the patient reflexively learns to take several deep breaths when an incident occurs, and to return to sleep. It has been unexpectedly discovered that this conditioned response to the alarm decreases or eliminates sleep apnea over a period of time during which the apparatus and method of the present invention is in use. This method of monitoring for the onset of sleep apnea and briefly arousing the patient from sleep on a regular and continuous basis is a form of biofeedback that is used to treat sleep apnea. The resulting reduction or elimination of the sleep apnea condition in the patient is one object of the present invention.

Figure 1:
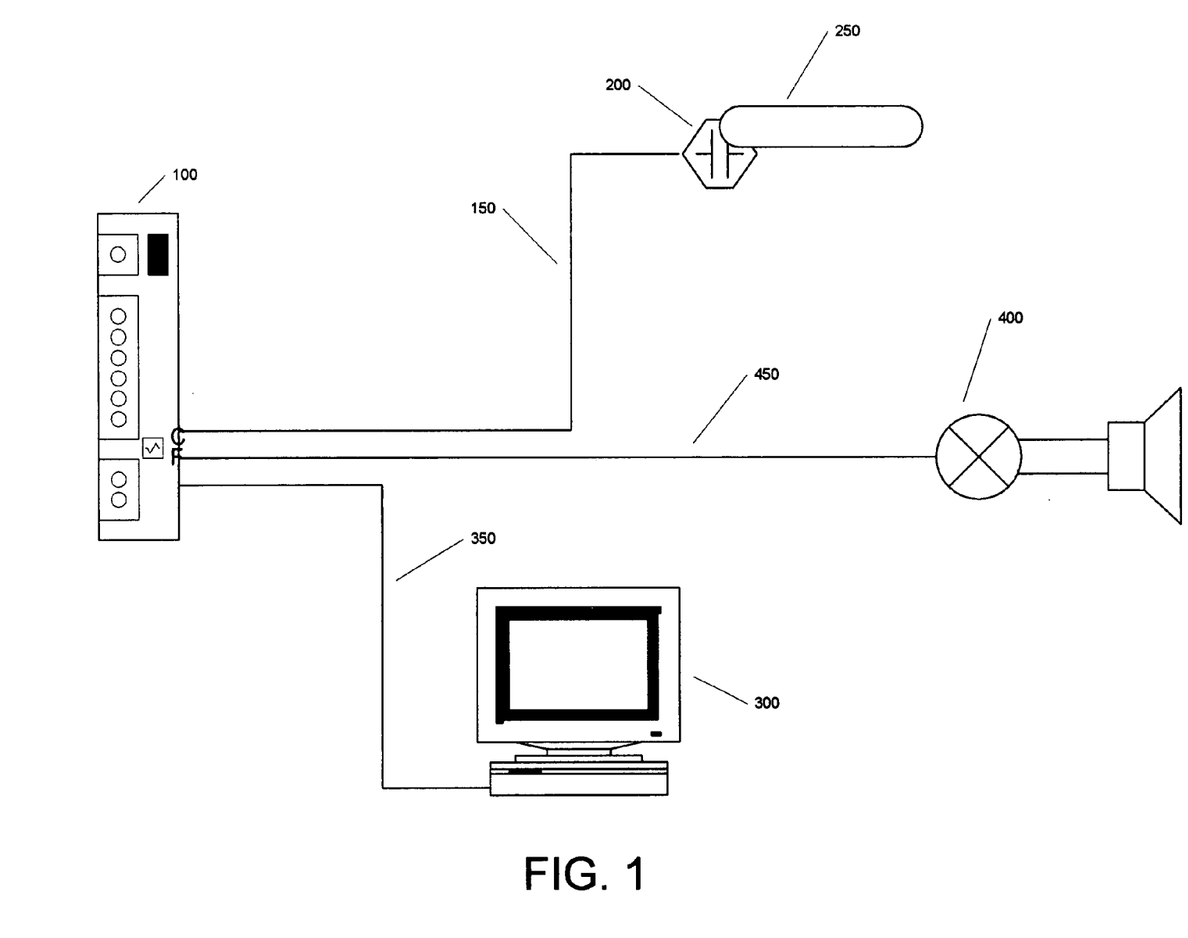
FIG. 1 is a schematic block diagram of the present invention.

Referring to the drawings, FIG. 1 is a functional block diagram of an apparatus of the present invention. In the embodiment depicted, a Pulse Oximeter 100 is connected to a probe 200 by way of a transmission path 150. In some embodiments of the present invention, the transmission path 150 may be a wire or a cable. In some embodiments of the present invention, the transmission path 150 may be a wireless link. Wireless links are known to those skilled in the art, and are used in baby monitors, wireless keyboards and mice for computers, wireless garage door openers, wireless remote car door openers, and the like. An example of a wireless link is described in U.S. Pat. No. 6,721,611 entitled "Antenna System and Apparatus for Radio-Frequency Wireless Keyboard", U.S. Pat. No. 6,507,763 entitled "Antenna System and Apparatus for Radio-Frequency Wireless Keyboard" and U.S. Pat. No. 6,138,050 entitled "Antenna System and Apparatus for Radio-Frequency Wireless Keyboard", the entire disclosures of which are incorporated herein by reference. The use of a wireless link as the transmission path 150 provides for comfortable sleeping conditions, free of wires, cables, and other obstructions. The use of a wireless link as the transmission path 150 will also reduce false alarm conditions caused by the probe 200 being pulled from the patient when connected by a wire or a cable. The probe 200 is attached to the patient's finger, toe, or earlobe 250, and provides monitoring signals to the Pulse Oximeter 100. The Pulse Oximeter 100 provides for non-invasive monitoring of the percentage of Hemoglobin (Hb) that is oxygen saturated. Pulse Oximeters have been described in several patents. See, for example, U.S. Pat. No. 5,190,038 entitled "Pulse Oximeter With Improved Accuracy and Response Time" by Polson and Morris, the entire disclosure of which is herein incorporated by reference.

The Pulse-Oximeter 100 works by measuring the absorption of light at two different wavelengths. The probe 200 emits two wavelengths of light in both the red and the infrared spectra (commonly 650 nm and 805 nm). The probe is attached to a patient's finger, toe or earlobe 250. The two wavelengths of light are partially absorbed by the hemoglobin present in the blood circulating in the finger, toe or earlobe 250. The absorption of the two wavelengths of light differ depending on the amount of oxygen that is contained in the hemoglobin. Bouguer and Lambert observed that the transmittance of light through an absorbing material decreases exponentially with an increase in the light path through the absorbing material. Beer and Bernard further observed that the concentration of a substance in solution is directly related to the absorbance of light therein. A combination of these two discoveries is known as Beer's Law. Beer's law states that an equal thickness of an absorbing material will absorb a constant fraction of the energy incident upon it. Stated as the Beer-Lambert equation:

$$A = \epsilon bc$$

Where A is absorbance;
$\epsilon$ is the molar absorptivity with units $L\ mol^{-1}\ cm^{-1}$;
b is the path length of the sample in cm.;
and c is the concentration of the absorbing material in solution, expressed in $mol\ L^{-1}$.

The optical properties of hemoglobin have been well established. Hemoglobin is a protein and the main component of red blood cells. Hemoglobin transports oxygen from the lungs to the surrounding tissues of the body. Oxygen saturation is the ratio of the amount of oxygen bound to hemoglobin to the total oxygen capacity of the hemoglobin. There are 4 basic forms of hemoglobin. If the hemoglobin molecule is bound to oxygen, the form is oxy-hemoglobin ($HbO_2$). If the hemoglobin molecule is bound to carbon dioxide, the form is carboxy-hemoglobin ($HbCO_2$). If the hemoglobin molecule is bound to nothing the form is deoxy-hemoglobin, also known as reduced hemoglobin (RHb). If the hemoglobin molecule has decomposed, the form is met-hemoglobin.

The coloration of hemoglobin varies substantially depending upon its form. Oxy-hemoglobin is bright red, resulting in the bright red appearance of oxygenated arterial blood; carboxy-hemoglobin is dark red in color, resulting in the dark red appearance of deoxygenated venous blood. Hence the presence and proportions of oxy-hemoglobin and carboxy-hemoglobin in blood is easily measured by optical means, and such measurement may be used as an indicator of overall blood oxygen content.

Referring again to FIG. 1, the mesurement probe 200 for pulse oximeter 100 contains two light sources (not shown) and two photodetectors (not shown). Examples of pulse oximeters include the Nonin Medical Series 8600 and other pulse oximeters manufactured by Nonin Medical, Inc. Another example of a pulse oximeter is the OxiMax™ N-595 Pulse Oximeter by Nellcor, as well as other pulse oximeters manufactured by Nellcor. In FIG. 1, the probe 200 emits light from these two sources into the finger, toe, or earlobe tissue 250 to which the probe 200 is attached. Some portion of the light from these two sources is absorbed in the tissue 250. The amount of absorbed light at each of the two wavelengths depends upon the composition of the hemoglobin present in the blood in the tissue 250. A remaining portion of the light from the two sources is transmitted back through the tissue 250 to the photodetectors in probe 200.

These photodetectors detect the transmitted light from each of the respective light sources, and amplify the received signals through a series of filters, amplifiers and processors. The Beer-Lambert equation is applied using a microprocessor contained in the pulse oximeter 100 to determine forms of hemoglobin in the blood and hence the concentration of oxygen in the blood. This measurement process using spectrophotometry is well known to those skilled in the art.

An additional capability of the pulse oximeter 100 is a pulse reading. The pulse is calculated in the pulse oximeter 100 by optically measuring the change in diameter of the vessel wall that occurs during each heart beat. The vessels are elastic, and the diameter of the vessel, and thus the optical path length, changes with every heart beat.

The pulse oximeter 100 is connected to an alarm 400 via transmission path 450. In some embodiments of the present invention, the transmission path 450 may be a wire or a cable. In some embodiments of the present invention, the transmission path 450 may be a wireless link to provide an audible, visual or sensory alarm condition to a remote location. Wireless links for remote alarms are known to those skilled in the art. Examples of wireless links include remote garage door openers, remote car door openers, wireless burglar alarm systems, and the like. The alarm 400 can be audible, visual, or a sensory alarm such as a vibrating alarm used to awaken deaf individuals. The alarm 400 may be contained within the pulse oximeter 100 or be external to the pulse oximeter.

The alarm is activated by way of threshold settings in the pulse oximeter 100. The threshold settings may also be set external to the pulse oximeter and used as a secondary method of activating the alarm. The threshold settings are programmable, and can be set by a physician, a technician, the patient, or an individual familiar with the medical condition of the patient. The threshold settings will activate the alarm 400 when the patient's percentage of blood oxygen level, or pulse rate, crosses a predetermined value. This event is indicative of the onset of sleep apnea. The alarm serves to briefly awaken the individual and to mitigate the apnea event.

It has been discovered by the inventor that the repetitive arousal from sleep at the onset of a sleep apnea event is a form of biofeedback and conditioning. This conditioned response over time serves to decrease the frequency of sleep apnea, as well as related arrhythmia and partial epilepsy. This biofeedback process has also been discovered to eliminate sleep apnea entirely. It is also known to those skilled in the art that sleep apnea may, in some cases, be related to certain forms of arrhythmia and, in some cases, partial epilepsy. The invention will also eliminate certain forms of arrhythmia and partial epilepsy.

It is a further object of the present invention to provide a method to determine and optimize the thresholds upon which the alarm 400 will activate upon detection of an apnea related event. The optimization of the blood oxygen level and pulse rate thresholds to the patient serves to reduce the occurrence of both false alarms as well as no alarm conditions. The present invention may contain an external computer or recording device 300 that will log and process blood oxygen levels and pulse rates during sleep. The computer or recording device 300 is connected to the pulse oximeter 100 with a cable 350 to allow for the transfer of blood oxygen level data and pulse rate data from the pulse oximeter 100 to the computer or recording device 300. The computer or recording device 300 will collect and process the pulse oximeter data, and may contain software programs, algorithms, or routines that will determine optimal alarm threshold levels by which to awaken the patient at the onset of an apnea event.

Figure 1A:
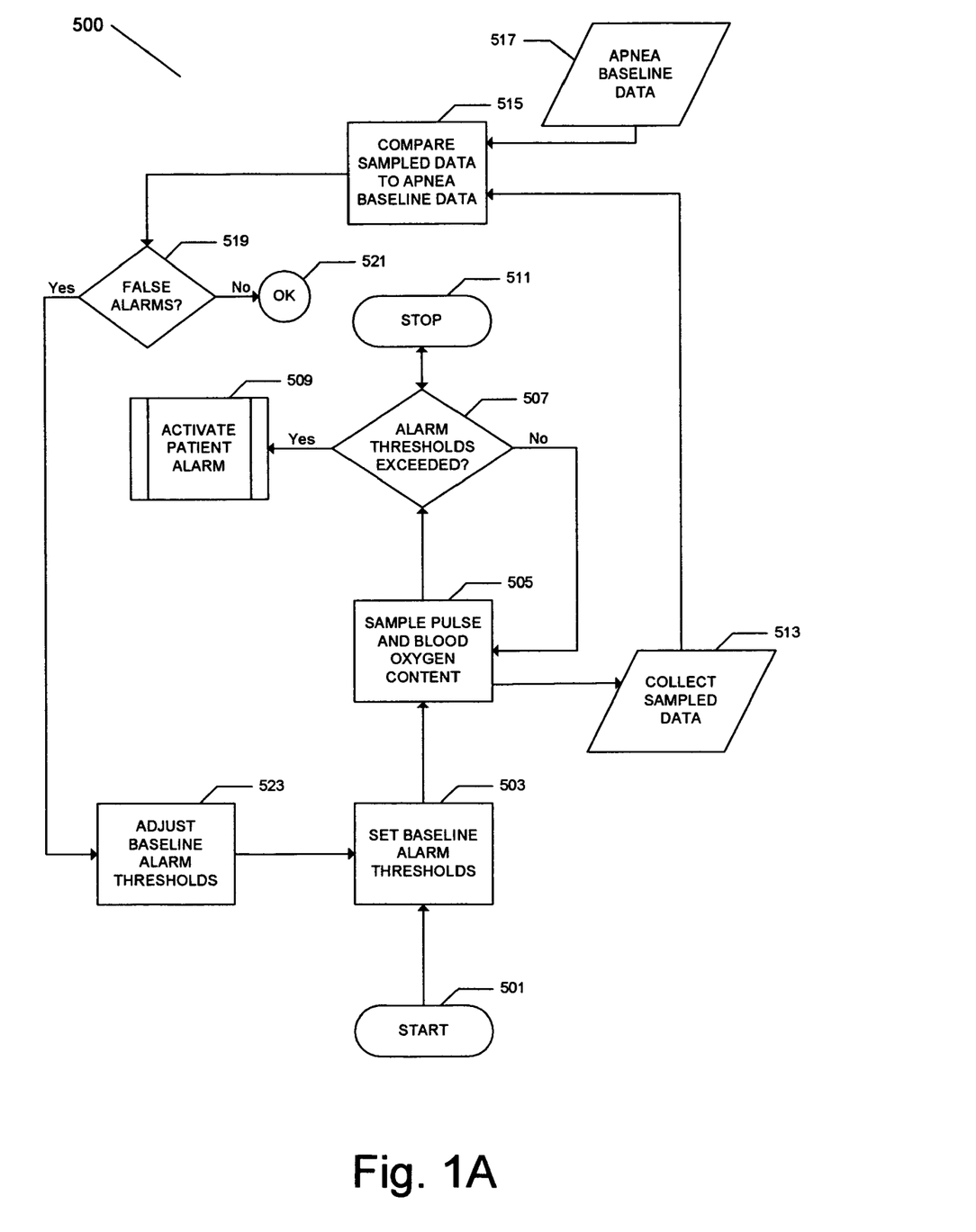
FIG. 1A is a flowchart of a software method of the present invention.

Referring now to FIG. 1A, a flowchart of a software program of the present invention is shown. In one embodiment of the present invention, the software program may reside within the pulse-oximeter. In other embodiments of the present invention, the software program may reside in a peripheral device, a computer, or a computing appliance. The software program uses historical data collected by the pulse-oximeter to optimize the detection of sleep apnea, and reduce the occurrence of false alarms. The method of optimizing the detection of sleep apnea through the use of historical data that is specific to the patient, and providing an alarm based on alarm threshold values derived from the historical data provides for an improved method of treating sleep apnea.

At the start 501 of the software program 500, baseline alarm thresholds 503 are set. The baseline alarm thresholds 503 are values at which an alarm is activated. These values are determined by a physician or medical practitioner, and may be changed based on patient specific information and treatment regimen. The baseline alarm thresholds 503 are set for both the blood oxygen level of the patient and the heart rate of the patient. The baseline alarm thresholds 503 may be entered manually by a physician or other medical practitioner, or the baseline alarm thresholds 503 may, in some embodiments, be set within the software program 500.

Once the baseline alarm thresholds 503 are set, the software program 500 begins to sample pulse and blood oxygen content 505. Pulse values and blood oxygen content values are collected with an external device such as a pulse-oximeter and transferred to the software program 500 using data transfer techniques known to those skilled in the art. The software program 500 also collects sampled data 513 that contains pulse values and blood oxygen content values. The sampled data 513 is stored in a file system or a database using techniques known to those skilled in the art.

The software program 500 will compare the sampled data 513 to apnea baseline data 517. Apnea baseline data 517 may, in some embodiments, contain pulse values and blood oxygen content values that are provided through the guidance of a physician or other medical practitioner. The apnea baseline data 517 provides pulse values, blood oxygen content values, and other medical data that indicates the onset of sleep apnea in a patient. The apnea baseline data 517 may, in some embodiments, be taken from polysomnographic readings of the patient. In other embodiments, the apnea baseline data 517 may be taken from a population of patients, and may, in some embodiments, be taken from statistically derived data. By way of example, and not limitation, apnea baseline data 517 may be derived from the "Sleep Heart Health Study: design, rationale and methods" by Quan, Howard, Iber, Kiley, Nieto, O'Connor, Rapoport, Redline, Robbins, Samet and Wahl in the December 1997 issue of Sleep. Other sources of apnea baseline data 517 will be evident and known to those skilled in the art. In step 515, the sampled data 513 is compared to apnea baseline data 517 to determine the occurrence of false alarms during a specified time period. If false alarms 519 are indicated through step 515, adjustments are made to baseline alarm thresholds in step 523. The adjustments may, in some embodiments, be made incrementally to ensure that a sleep apnea event is properly detected. If no false alarms 519 are detected, or a small number of false alarms are detected that are within an acceptable margin of error that has been pre-defined either within the software program 500 or by a physician or medical practitioner, there will be no adjustments made to the baseline alarm thresholds by way of step 523, and the outcome will be an OK status 521.

Returning now to step 505, sample pulse and blood oxygen content, the software program 500 is continually checking in step 507 to determine if the alarm thresholds are exceeded. If the alarm thresholds have not been exceeded in step 507, sampling of pulse and blood oxygen content continues with no ancillary processes started. In step 507, if an alarm threshold is exceeded, an ancillary process is started that activates a patient alarm 509. The alarm will briefly cause the patient to briefly awaken the patient will take several deep breaths and return to sleep, thus ceasing the apnea condition. This process of monitoring, alarming, and adjusting alarm thresholds continues throughout the treatment regimen; the result of said process being a gradual reduction in the frequency and quantity of apnea events.

Figure 2:
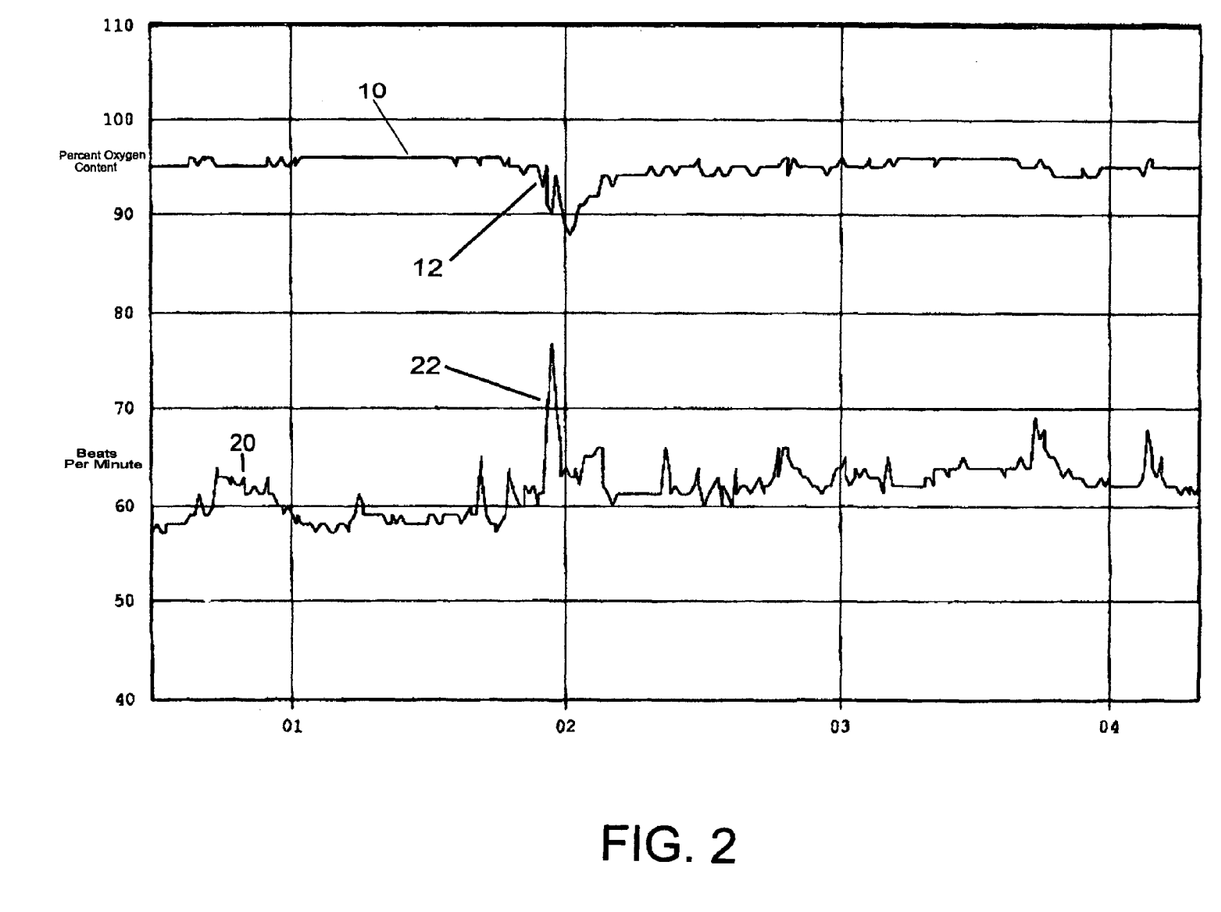
FIG. 2 is a trace of blood oxygen level and pulse prior to, during, and after sleep apnea.
Figure 3:
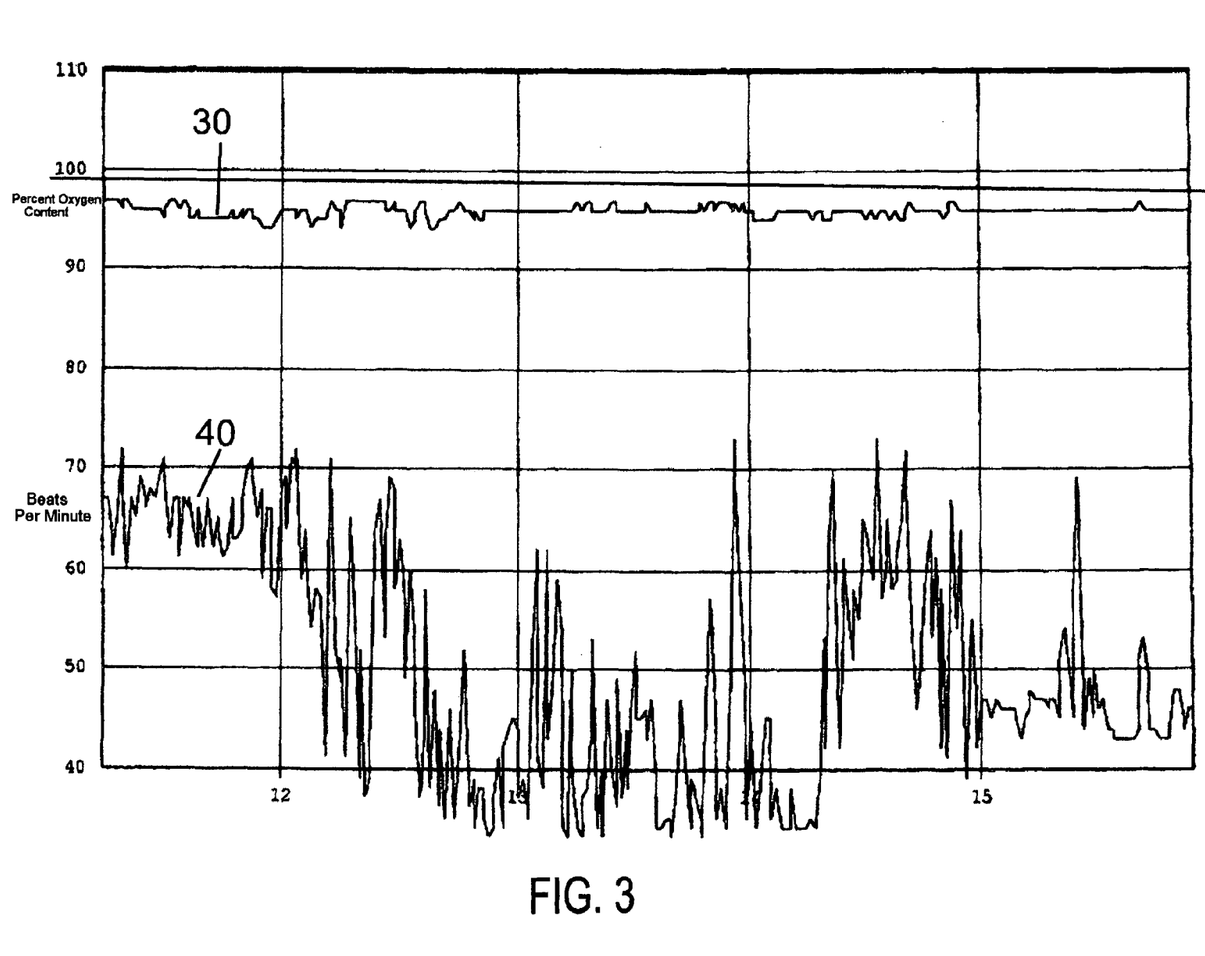
FIG. 3 is a trace of blood oxygen level and pulse that shows arrhythmia prior to treatment with the invention.
Figure 4:
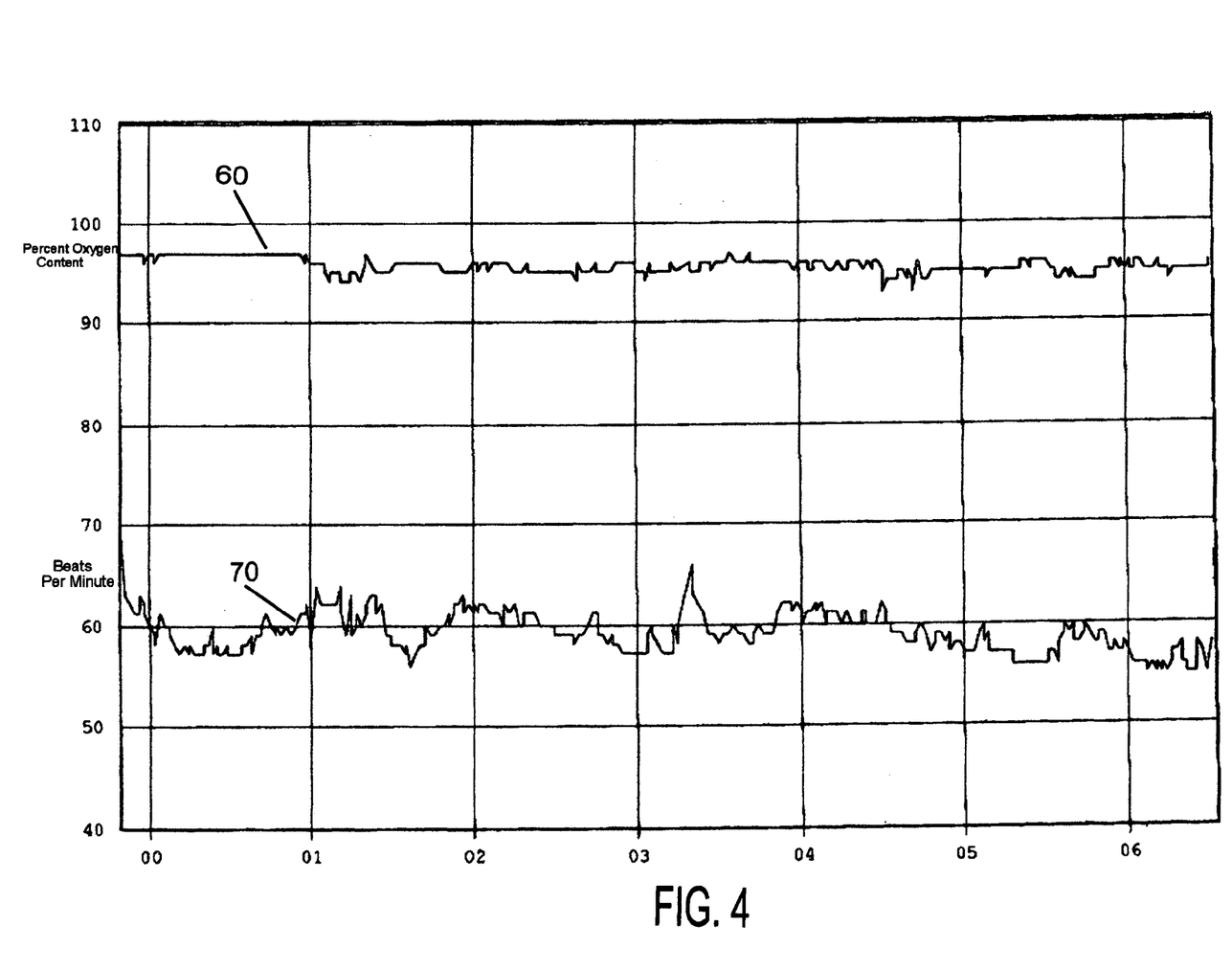
FIG. 4 is a trace of blood oxygen level and pulse during sleep; after treatment using the present invention.

FIGS. 2, 3 and 4 illustrate graphically the results of this method of treatment. FIG. 2 represents a plot of both blood oxygen level 10 and pulse rate 20 during a period of sleep by a patient. The graph was taken using the computer recorder 300 of the disclosed invention. Both traces shown in the plot are with respect to hours. Blood oxygen level 10 and pulse rate 20 are at levels indicative of normal restful sleep at about hour 01. As is evident from the plot, shortly before hour 02 the patient entered into a period of sleep apnea. This is evident from the increased pulse rate 22 and decrease in blood oxygen level 12. At the onset of the sleep apnea event, the disclosed invention detected the onset of sleep apnea, and activated the alarm 400. The patient awoke briefly, took several deep breaths, and returned to sleep. The apnea event was mitigated, and pulse rate 20 and blood oxygen level 10 returned to levels indicative of normal restful sleep.

The apparatus of the invention, and the method of the invention were used nightly by this patient. A continued decrease in the frequency of the apnea events was noted over the course of several months, with an almost total elimination of sleep apnea events after three months of use of the disclosed invention.

FIG. 3 is a plot of both blood oxygen level 30 and pulse rate 40 during an arrhythmia event. These arrhythmia events were common during the period prior to the use of the invention. The graph was taken using the computer recorder 300 of the disclosed invention. Both traces shown in the plot are with respect to minutes.

FIG. 4 is a plot of both blood oxygen level 60 and pulse rate 70 during a session of sleep by the patient after treatment of sleep apnea with the disclosed invention for a period of 30 days. Applicants believe that given the variability of potential patients heath profiles, treatment times may vary from about seven days to about ninety days. The graph was taken using the computer recorder 300 of the disclosed invention. Both traces shown in the plot are with respect to hours. As is evident from the plot, the blood oxygen level and pulse rate were maintained within normal levels, and there is no indication of the onset of sleep apnea at any time during the sleep period. The patient enjoyed a restful session of sleep, in contrast to the frequently disrupted sleep which occurred prior to treatment of the patient with the apparatus and methods of the present invention.

This invention may also be used as a treatment for other sleep related disorders such as snoring, sleep walking (somnambulism), sleep talking, periodic leg movements in sleep (PLMS), sleep terrors, bruxism or the alpha-EEG anomaly associated with fibromyalgia. This invention may also be used to reduce the incidence of apnea events in newborns and infants, and may be used to monitor for, and prevent, Sudden Infant Death Syndrome (SIDS).

It is, therefore, apparent that there has been provided, in accordance with the various objects of the present invention, an apparatus and a method for the treatment of sleep apnea, arrhythmia, and partial epilepsy. While the various objects of this invention have been described in conjunction with preferred embodiments thereof, it is evident that many alternatives, modifications, and variations will be apparent to those skilled in the art. Accordingly, it is intended to embrace all such alternatives, modifications and variations that fall within the spirit and broad scope of the appended claims.

What is claimed is:

1. An apparatus for the treatment of sleep related disorders in a patient, said apparatus comprising:
   a. a patient probe for sensing and conveying data indicative of pulse rate and blood oxygen content to a device;
   b. a device connected to the patient probe for measuring pulse rate and blood oxygen content of a patient;
   c. a means for detecting the onset of a sleep related disorder using pulse rate and blood oxygen content information as measured by the device;
   d. an alarm for modifying the patient's sleep that is activated upon an indication of the onset of a sleep related disorder; and
   e. a computer including a computer program, wherein said computer program extracts data from said device, compares said data to historical baseline data, and dynamically adjusts threshold values of said pulse rate and said blood oxygen content at which to activate said alarm.

2. The apparatus of claim 1 wherein the device is a pulse-oximeter.

3. The apparatus as recited in claim 1, wherein said alarm is an audible alarm.

4. The apparatus as recited in claim 1, wherein said alarm is a visual alarm.

5. The apparatus as recited in claim 1, wherein said alarm is a mechanical alarm.

6. The apparatus as recited in claim 1, wherein said alarm is in wireless communication with said device.

7. The apparatus as recited in claim 1, wherein said patient probe is in wireless communication with said device.

* * * * *